United States Patent
Carlucci et al.

(10) Patent No.: US 12,090,157 B2
(45) Date of Patent: Sep. 17, 2024

(54) NON-INVASIVE PET IMAGING OF CDK4/6 ACTIVATION IN CANCER

(71) Applicants: New York University, New York, NY (US); Memorial Sloan Kettering Cancer Center, New York, NY (US)

(72) Inventors: Giuseppe Carlucci, New York, NY (US); Thomas Reiner, New York, NY (US)

(*) Notice: Subject to any disclaimer, the term of this patent is extended or adjusted under 35 U.S.C. 154(b) by 329 days.

(21) Appl. No.: 17/246,291

(22) Filed: Apr. 30, 2021

(65) Prior Publication Data

US 2021/0338670 A1    Nov. 4, 2021

Related U.S. Application Data

(60) Provisional application No. 63/018,303, filed on Apr. 30, 2020.

(51) Int. Cl.
*A61K 31/506* (2006.01)
*G01N 33/574* (2006.01)

(52) U.S. Cl.
CPC ..... *A61K 31/506* (2013.01); *G01N 33/57415* (2013.01)

(58) Field of Classification Search
CPC ........................ A61K 31/506; G01N 33/57415
See application file for complete search history.

(56) References Cited

PUBLICATIONS

Gan et al. "Preparation and evaluation of 99mTc-labeled HYNIC-palbociclib analogs for cyclin-dependent kinase 4/6-positive tumor imaging," European Journal of Medicinal Chemistry vol. 188, Feb. 15, 2020, 112032, pp. 1-9 (Year: 2020).*
Amano et al. "In Vivo Comparison of PET and SPECT Radiopharmaceuticals in Detecting Breast Cancer," The Journal of Nuclear Medicine vol. 39 No. 8 Aug. 1998, pp. 1424-1427 (Year: 1998).*
Ramos et al. Noninvasive PET Imaging of CDK4/6 Activation in Breast Cancer, The Journal of Nuclear Medicine vol. 61 No. 3 Published online Sep. 3, 2019. (Year: 2019).*

* cited by examiner

*Primary Examiner* — Jeffrey S Lundgren
*Assistant Examiner* — William Y Lee
(74) *Attorney, Agent, or Firm* — Hodgson Russ LLP

(57) ABSTRACT

Disclosed are compounds having the following structure:

$$\text{CDK-L-(X)}_n,$$

where CDK is a CDK4/6 inhibitor group, L is a linking group, X is a radiolabel or hydrogen, n is 1, 2, 3, 4, or 5, and when there are a plurality of X groups, at least one X is a radiolabel. Also described are methods of making and using the compounds. The compounds may be used in PET imaging to quantify CDK4/6 expression in cancers and to treat cancer patients exhibiting tumors which express CDK4/6.

18 Claims, 7 Drawing Sheets

NON-INVASIVE PET IMAGING OF CDK4/6 ACTIVATION IN CANCER

CROSS REFERENCE TO RELATED APPLICATION

This application claims priority to U.S. Provisional Patent Application No. 63/018,303, filed Apr. 30, 2020, the disclosure of which is incorporated herein by reference.

STATEMENT REGARDING FEDERALLY SPONSORED RESEARCH

This invention was made with government support under contract no. P41 EB017183 awarded by the National Institutes of Health. The government has certain rights in the invention.

BACKGROUND OF THE DISCLOSURE

The cell cycle is a progression of four distinct phases (G1, S, G2, M) that cells use to maintain the integrity of their genomes. Sophisticated cell cycle pathways and cell cycle arrest proteins are used to remediate DNA damage, to efficiently control the cell cycle and DNA replication, and to trigger DNA repair. Alterations in the cell cycle and uncontrolled proliferation are well known hallmarks of cancer. Cyclin Dependent Kinases 4/6 (CDK4/6) are two apical kinases that control the cell cycle by arresting the progression in case of DNA damage. Subsequent to cell damage, cycD1-CDK4/6 complex arrests the cell cycle progression in G1 to limit the proliferation of the DNA-damaged cell (Musgrove et al., *Nat Rev Cancer.* 2011; 11:558-572). The dysregulation of the cycD1-CDK4/6 axis appears to be an early step in cancer pathogenesis and cycD1 overexpression is shown as early as ductal carcinoma in both, in situ and in metastatic lesions (Finn et al., *Breast Cancer Res.* 2016; 18:17, Musgrove et al., *Nat Rev Cancer.* 2011; 11:558-572). Notably, amplification of genes encoding D-type cyclins is commonly observed in human cancer and correlates with increased levels of cyclin D protein. A major target of CDK4 and CDK6 during cell-cycle progression is the retinoblastoma protein (Rb). CDK4/6-cycD1 complexes phosphorylate Rb. When Rb is phosphorylated, it dissociates from the E2F family that enable cell cycle progression to the S phase. Selective inhibitors act on CDK4/6 kinases, dephosphorylate Rb and stall the cell-cycle progression in G1. This action inhibits the proliferation of cancer cells and triggers the DNA-damage repair. Hence, it is intuitive that efficient inhibition of CDK4/6 can enhance and amplify the chemotherapeutic effects of therapies aimed at targeting the cell cycle proliferation, checkpoints and arrest.

Amplification of CDK4/6 and cycD1 has been reported in a significant number of cancers and the overexpression of cycD1 was observed in >60% of all breast cancers (Hamilton et al., *Cancer Treat Rev.* 2016; 45:129-138, Bartkova et al., *Int J Cancer.* 1994; 57:353-361, Dickson et al., *Cancer Lett.* 1995; 90:43-50, Yu et al., *Nature.* 2001; 411:1017-1021). Furthermore, amplification and overexpression of cycD1 and CKD4/6 has been described in patients with head and neck cancer (Akervall et al., *Cancer.* 1997; 79:380-389), non-small-cell lung cancer (Betticher et al., *Br J Cancer.* 1996; 73:294-300), melanoma (Bleeker et al., *Hum Mutat.* 2009; 30:E451-459, Curtin et al., *N Engl J Med.* 2005; 353:2135-2147, Freedman et al., *Am J Pathol.* 2011; 178: 2513-2522) and glioblastoma (Brennan et al., *Cell.* 2013; 155:462-477). Gene amplification of cycD1 was found to be most frequent in luminal A, B and HER2 enriched breast cancer subtypes (frequencies of alteration: 29%, 58%, and 38%, respectively) (Finn et al., *Breast Cancer Res.* 2016; 18:17). Similarly, amplifications of CDK4/6 were more common in the luminal A, B and human epidermal growth factor receptor 2 ($HER_2$) enriched subgroups (14%, 25%, and 24%, respectively) (Finn et al., *Breast Cancer Res.* 2016; 18:17). Moreover, in patients with luminal estrogen receptor (ER)-positive breast cancer, which represents approximately 75% of all breast cancers, cycD1-CDK4/6 is expressed at a high-level (VanArsdale et al., *Clin Cancer Res.* 2015; 21:2905-2910).

SUMMARY OF THE DISCLOSURE

The present disclosure provides compositions and methods for PET imaging to quantify CDK4/6 expression in cancers. For example, PET imaging to quantify CDK4/6 may be carried out in cancers that are characterized by overexpression of CDK4/6. An example is ER-positive HER2-negative breast cancer.

In an aspect, the disclosure provides a novel PET imaging agent to quantify CDK4/6 expression. In an embodiment, the agent is trans-fluorinated $^{18}$F-CDKi.

In an aspect, the disclosure provides pharmaceutical compositions comprising the $^{18}$F-CDKi, which can be administered to a subject.

In an aspect, the disclosure provides a method for identifying suitability of cancer patients for treatment with CDK4/6 inhibitors. For example, the present composition may be administered to an individual who is diagnosed with cancer and PET imaging can be carried out to determine if there is accumulation of the a compound of Formula 1 in the tumor of the individual. If there is accumulation, the individual is considered suitable for treatment with CDK4/6 inhibitors and may be administered such inhibitors (including the compound of Formula 1, with or without the radiolabel), and if there is no clinically significant accumulation, then the individual is considered to be a candidate for a treatment other than a CDK4/6 inhibitor.

In an aspect, the disclosure provides methods for monitoring the progression of cancer or efficacy of cancer treatments. For example, the present compositions and methods may be used for accurate assessment of functional CDK4/6 expression in breast cancer development. In an embodiment, the present compositions and methods can be used to monitor cancer progression and/or to monitor and develop CDK4/6 based treatments. These methods may be applied to any cancer, including cancers that are characterized by overexpression of CDK4/6. An example is ER-positive HER2-negative breast cancer.

DETAILED DESCRIPTION OF THE DISCLOSURE

Figure 1:
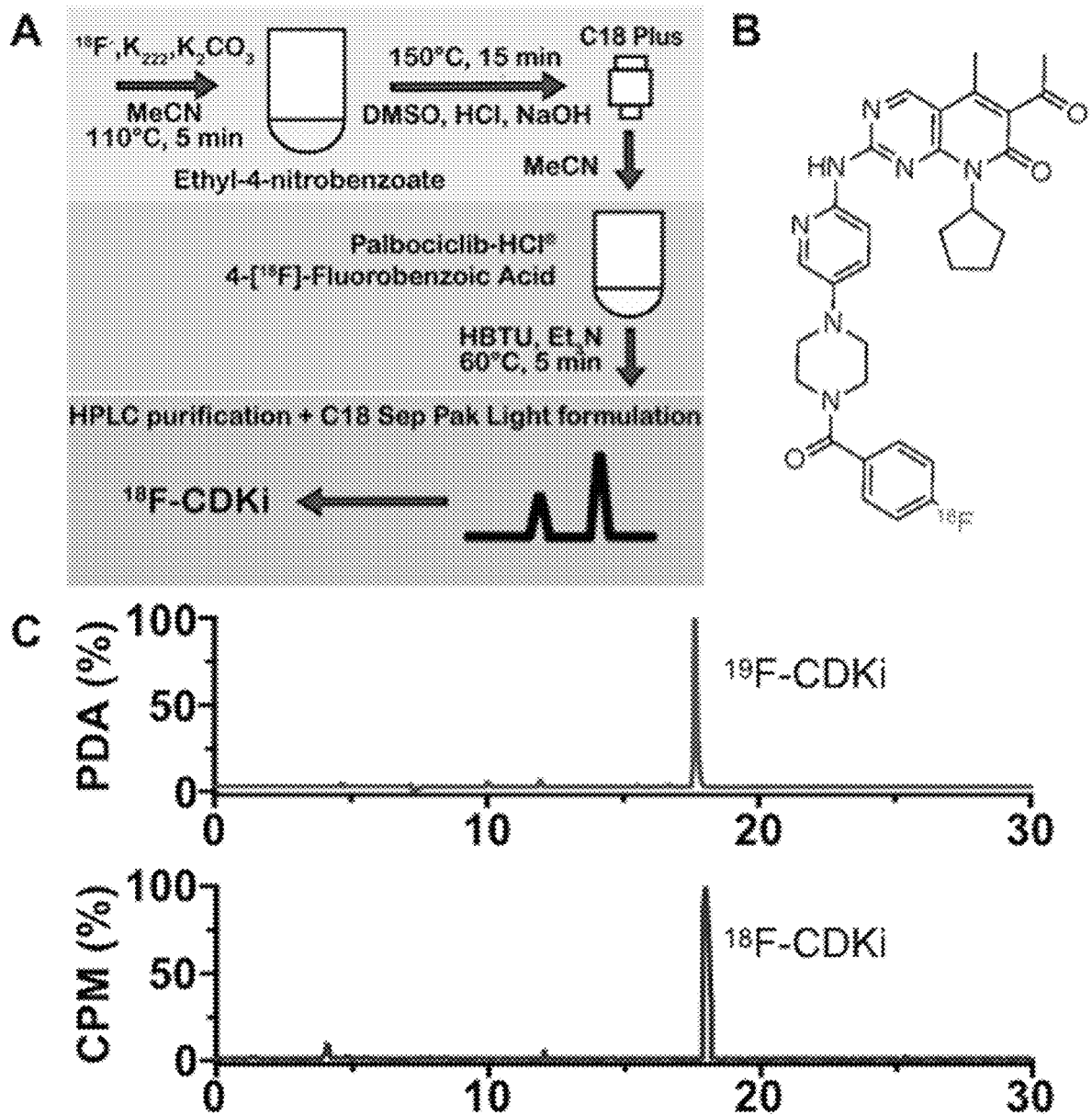
FIG. 1 shows $^{18}$F-CDKi radiochemistry and production method (A). The chromatograms represent a co-injection of $^{18}$F-CDKi (B) with $^{19}$F-CDKi and show the successful synthesis and purity of the PET tracer (C).

The present disclosure provides compositions and methods for quantifying CDK4/6 expression in cancers, such as ER-positive HER2-negative breast cancer by PET imaging.

Every numerical range given throughout this specification includes its upper and lower values, as well as every narrower numerical range that falls within it, as if such narrower numerical ranges were all expressly written herein.

Throughout this application, the singular form encompasses the plural and vice versa. All sections of this application, including any supplementary sections or figures, are fully a part of this application.

As used therein, the term "treatment" as used herein refers to alleviation of one or more symptoms or features associated with the presence of the particular condition or suspected condition being treated. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent.

As used herein, the term "effective amount" means an amount that is sufficient, when administered to a population suffering from or susceptible to a disease, disorder, and/or condition in accordance with a dosing regimen, to treat the disease, disorder, and/or condition. In some embodiments, an effective amount is one that reduces the incidence and/or severity of, and/or delays onset of, one or more symptoms of the disease, disorder, and/or condition. Those of ordinary skill in the art will appreciate that the term "effective amount" does not require successful treatment be achieved in a particular individual. Rather, an effective amount may be that amount that provides a particular desired pharmacological response in a significant number of subjects when administered to patients in need of such treatment. It is specifically understood that particular subjects may, in fact, be "refractory" to an "effective amount." To give but one example, a refractory subject may have a low bioavailability such that clinical efficacy is not obtainable. In some embodiments, reference to an effective amount may be a reference to an amount as measured in one or more specific tissues (e.g., a tissue affected by the disease, disorder or condition) or fluids (e.g., blood, saliva, serum, sweat, tears, urine, etc.). Those skilled in the art will appreciate that, in some embodiments, an effective amount may be formulated and/or administered in a single dose. In some embodiments, an effective amount may be formulated and/or administered in a plurality of doses, for example, as part of a dosing regimen.

As used herein, unless otherwise indicated, the term "group" refers to a chemical entity that is monovalent (i.e., has one terminus that can be covalently bonded to other chemical species as in a methyl or phenyl group), divalent, or polyvalent (i.e., has two or more termini that can be covalently bonded to other chemical species as in a methylene or phenylene group). The term "group" also includes radicals (e.g., monovalent radicals and multivalent radicals, such as, for example, divalent radicals, trivalent radicals, and the like).

In an aspect, the present disclosure provides compounds (e.g., radiolabeled inhibitors of CDK4/6) that may be used for non-invasive imaging. "Non-invasive imaging" as used herein refers the process of imaging an individual without introducing an instrument (e.g., probe) into the body of the individual. Examples of non-invasive imaging, include, but are not limited to, positron emission tomography (PET).

An example of an inhibitor of CDK4/6 is palbociclib. Other examples include ribociclib and abemaciclib. In an embodiment, the disclosure provides a radiolabeled derivative of a CDK4/6 inhibitor, such as palbociclib, ribociclib or abemaciclib that is suitably radiolabeled for non-invasive imaging, such as for PET imaging. For example, the palbociclib may be radiolabeled with a radioactive halide. In an embodiment, the palbociclib is radiolabeled with $^{18}$F.

In various examples, a compound (e.g., radiolabeled inhibitors of CDK4/6) has the following the structure:

$$\text{CDK-L-(X)}_n \qquad \text{(Formula 1)},$$

where CDK is a CDK4/6 inhibitor group, L is a linking group, X is a radiolabel or hydrogen, and n is 1, 2, 3, 4, or 5, and when n is 1, X is a radiolabel, and when n is 2-5, then at least one X is a radiolabel.

A CDK4/6 inhibitor group is formed from a CDK4/6 inhibitor. A CDK4/6 inhibitor group may be formed from palbociclib, ribociclib, abemaciclib, or the like. For example. a CDK4/6 inhibitor group has the following structure:

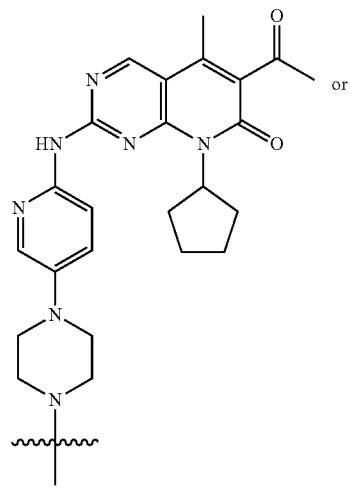

or

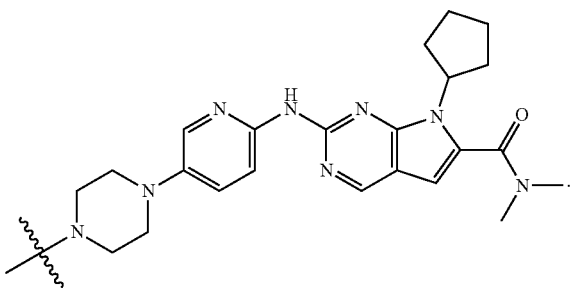

A linking group links a CDK4/6 inhibitor group to one or more radiolabels. A linking group may have the following structure:

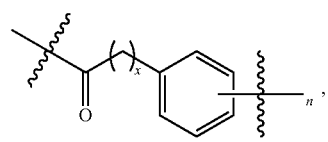

where n is 1, 2, 3, 4, or 5 and x is 0, 1, 2, 3, 4, 5, 6, 7, 8, 9, or 10. In various examples, a linking group has the following structure:

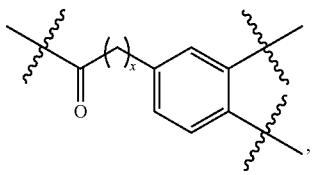

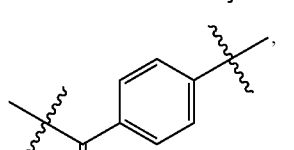

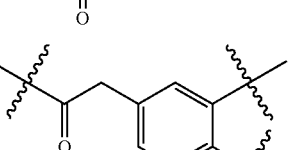

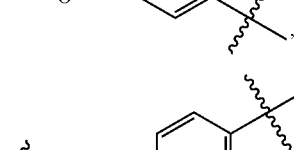

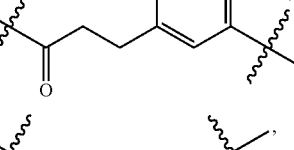, or

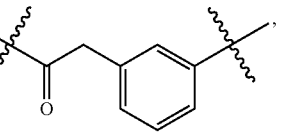

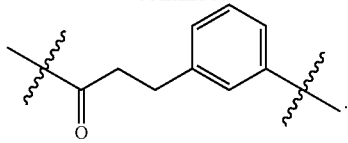.

The compounds may comprise various radiolabels. Non-limiting examples of radiolabels include: $^{123}$I, $^{124}$I, $^{125}$I, $^{131}$I, $^{211}$At, $^{18}$F and the like, and combinations thereof. In various examples, the radiolabel is $^{18}$F. In various other examples, a compound of the present disclosure may comprise additional radiolabels, such as, for example, but not limited to, $^{11}$C, $^{13}$N, $^{64}$Cu, $^{68}$Ga, and $^{76}$Br.

In various examples, L-(X)$_n$ has the following structure:

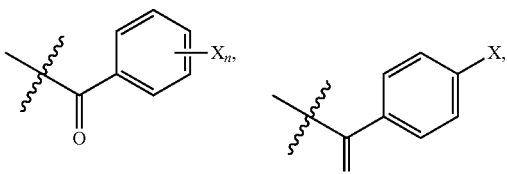

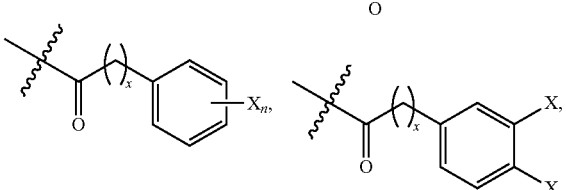

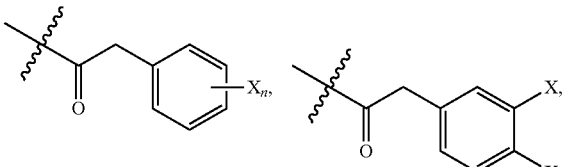

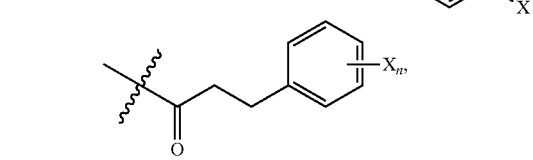

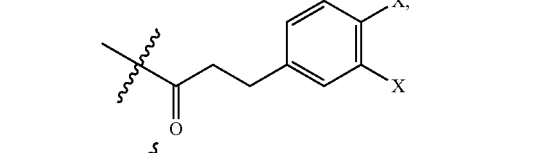

where X is a radiolabel (e.g., $^{123}$I, $^{124}$I, $^{125}$I, $^{131}$I, $^{211}$At, and $^{18}$F) or hydrogen, n is 1, 2, 3, 4, or 5, x is 1, 2, 3, 4, 5, 6, 7, 8, 9, or 10, and when n is 1, X is a radiolabel, and when n is 2-5, then at least one X is a radiolabel.

In various examples, a compound of the present disclosure has the following structure:

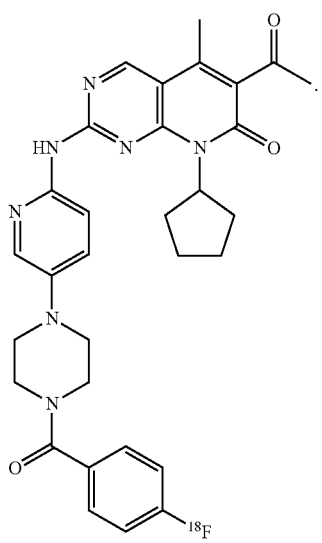 [SMILES: CC(=O)c1c(C)c2cnc(Nc3ccc(N4CCN(C(=O)c5ccc([18F])cc5)CC4)cn3)nc2n(C2CCCC2)c1=O]

In an aspect, this disclosure provides compositions comprising compounds of the present disclosure (e.g., radiolabeled inhibitors of CDK4/6). The compositions may be suitable for administration via any route. The compositions may comprise pharmaceutical carriers, excipients, buffers, and the like.

A composition may comprise additional components. For example, the composition comprises a buffer solution suitable for administration to an individual (e.g., a mammal such as, for example, a human or a non-human). An individual may be a subject. The buffer solution may be a pharmaceutically acceptable carrier.

A composition may include one or more standard pharmaceutically acceptable carrier(s). Non-limiting examples of compositions include solutions, suspensions, emulsions, solid injectable compositions that are dissolved or suspended in a solvent before use, and the like. Injections may be prepared by dissolving, suspending or emulsifying one or more of the active ingredient(s) in a diluent. Non-limiting examples of diluents include distilled water for injection, physiological saline, vegetable oil, alcohol, and the like, and combinations thereof. Further, a composition (e.g., a composition suitable for injection) may contain stabilizers, solubilizers, suspending agents, emulsifiers, soothing agents, buffers, preservatives, and the like. Compositions (e.g., compositions suitable for injection) may be sterilized in the final formulation step or prepared by sterile procedure. The composition may also be formulated into a sterile solid preparation, for example, by freeze-drying, and can be used after sterilized or dissolved in sterile injectable water or other sterile diluent(s) immediately before use. Non-limiting examples of pharmaceutically acceptable carriers can be found in: *Remington: The Science and Practice of Pharmacy* (2005) 21st Edition, Philadelphia, PA. Lippincott Williams & Wilkins.

Pharmaceutically acceptable compositions of the present disclosure may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of the present disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of the present disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of chemical entities of the present disclosure include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

Pharmaceutically acceptable compositions of the present disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions of the present disclosure can also formulated for oral administration. Such formulations may be administered with or without food. In some embodiments, pharmaceutically acceptable compositions of the present disclosure are administered without food. In other embodiments, pharmaceutically acceptable compositions of the present disclosure are administered with food.

The amount of chemical entities of the present disclosure that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific chemical entity employed, the age, body weight, general health, sex, diet, time of administration, rate of excretion, drug combination, and the judgment of the treating physician and the severity of the particular disease being treated. The amount of a chemical entity of the present disclosure in the composition will also depend upon the particular chemical entity in the composition.

In an aspect, this disclosure provides methods for identifying subjects that may be most suited (e.g., those subjects that benefit or benefit the most) from a therapy comprising CDK4/6 inhibitor. The method may comprise administering to the subject being considered for such therapy an effective amount of a compound of the present disclosure (e.g., a compound of Formula 1) or of a composition comprising a compound of the present disclosure, such as, for example, an effective amount of $^{18}$F-CDKi. By using imaging techniques, such as PET, it can be evaluated whether or not the a compound (e.g., $^{18}$F-CDKi) is accumulating in the tumor. If clinically significant amounts of compound (e.g., $^{18}$F-CDKi) are found to accumulate in the tumor (indicating expression of CDK4/6), the subject can be considered a suitable candidate for CDK4/6 inhibitor therapy, and thereafter can be administered an inhibitor of CDK4/6. The subject may be administered palbociclib or may be administered some other inhibitor of CDK4/6. If no clinically significant accumulation of the compound (e.g., $^{18}$F-CDKi) is observed, the subject is not administered a CDK4/6 inhibitor regimen. Rather, the subject can be administered an alternative therapy. For example, depending upon the status of HER2 or ER, a subject may be administered therapies comprising such as checkpoint inhibitors, mTor inhibitors (e.g., Everolimus), kinase inhibitors (e.g., Lapatinib, Neratinib, Tucatinib), P13K inhibitors (e.g., alpelisib), monoclonal antibodies (e.g., Trastuzumab, Pertuzumab), antibody-drug conjugates (e.g., Ado-trastuzumab emtansine, Fam-trastuzumab deruxtecan) and the like. In various embodiments, clinical significance may be calculated empirically based small molecule pharmacokinetic modeling. In various embodiments, accumulation that may be considered clinically significant may be at least 5, at least 10, at least 15, at least 20, at least 25, at least 30, at least 35, at least 40, at least 45, at least 50, at least 55, at least 60, at least 65, at least 70, or at least 75% higher than a background or reference tissue. For example, if cancer is suspected in one breast, the other breast may be used as a reference tissue to measure accumulation.

In an embodiment, the present compositions and methods can be used for evaluating subjects who are on CDK4/6 inhibitor therapy and who have developed resistance to such therapy. The method comprises administering to a subject who has developed resistance an effective amount of a radiolabeled CDK4/6 inhibitor (e.g., a compound of Formula 1) and determining if the inhibitor exhibits accumulation in the tumor. If no clinically relevant accumulation is detected, the subject may be administered an alternative breast cancer therapy as mentioned above. If accumulation is detected, the CDK4/6 inhibitor may be continued, but at an increased dosage or at a dosage modified to overcome the resistance. The continued administration may comprise the CDK4/6 inhibitor without the radiolabel or it may comprise the CDK5/6 inhibitor with the radiolabel or a combination thereof.

In embodiments, a compound of the present disclosure, such as, for example, $^{18}$F-CDKi, can be used to select patient responders or non-responders to CDK4/6 inhibitors. For example, $^{18}$F-CDKi might assess whether CDK or palbociclib treatment combinations are well tolerated, even without an increase of febrile neutropenia which is significantly more common in the palbociclib-containing combinations compared to hormonal therapy alone. Moreover, the compound, such as, for example, $^{18}$F-CDKi, can indicate whether treatments necessitate dose interruptions and reductions. Finally, the compound, such as, for example, $^{18}$F-CDKi may allow to study pharmacodynamic effects of lower doses of palbociclib. This can help to tailor a specific line of treatment in ER-positive HER2-negative breast cancer patients. For example, the compound may be used as a tracer, which might further be used as a tool to improve patients outcome or design a more personalized combination strategies.

$^{18}$F-CDKi combines high stability, fast penetration, high contrast and rapid washout properties with a remarkable in vitro and in vivo binding to CDK4/6. $^{18}$F-CDKi is cleared via hepatobiliary route. These results suggest that this probe could offer an early prognostic assessment of treatment response or acquired resistance to CDK4/6 inhibitors. Moreover, with a hybrid imaging technique, such as PET $^{18}$F-CDKi in combination with MRI, clinicians might have an alternative approach to tailor precise medical treatments and therapies based on patient CDK4/6 biomarker expression.

By using the compositions and methods of the present disclosure, an exact and accurate assessment of functional CDK4/6 expression in cancer development and progression and can be made and used to monitor CDK4/6 based treatment. Cancers that may be treated using the present compositions and methods include, but are not limited to, breast cancer, head and neck cancer, non-small cell lung cancer, melanoma, and glioblastoma. As described herein, the first in vitro experiment aiming to analyze pharmacokinetics (PK) and in vitro activity revealed that $^{18}$F-CDKi (based on Palbociclib, an FDA approved drug) can be a successful PET agent with nearly ideal imaging characteristics. $^{18}$F-CDKi is stable in vitro and in vivo and maintained a potent targeting affinity to CDK4/6. Cellular uptake experiments performed in a MCF-7 breast cancer cell line (ER-positive/HER$_2$-negative) demonstrated specific uptake. Similar significant uptake values were also observed in MCF-7 bearing mouse models. The strong activation of CDK4/6 in cancer cells in concert with its low activation in untransformed healthy cells (as resulted from our tumor-to-non-target tissue ratio calculations) makes $^{18}$F-CDKi an ideal imaging agent, first in its class, for CDK4/6 assessment. Data provided herein demonstrates $^{18}$F-CDKi can improve screening for breast cancer and selection of responders to CDK4/6 therapy. $^{18}$F-CDKi allows to quantify CDK4/6 activation (at a cellular level) and to assess CDK4/6 protein status in current translational cancer research.

In various embodiments, the present disclosure provides treating a disease or disorder characterized by overexpression of CDK4/6 in an individual in need of treatment comprising administering an effective amount compound according of the present disclosure (e.g., compound of Formula 1) or a composition of the present disclosure. In various examples, the disease or disorder is cancer. The cancer may be ER-positive and HER2-negative (e.g., ER-positive and HER2-negative breast cancer). The cancer may be breast cancer, head and neck cancer, non-small cell lung cancer, melanoma, glioblastoma, or a combination thereof. The cancer may be a tumor. The method may further comprise PET imaging.

In various embodiments, a method of the present disclosure comprises treating cancer by identifying an individual who has a tumor, where the tumor exhibits accumulation of a compound of the present disclosure e.g., a compound having the following structure: CDK-L-(X)$_n$, where CDK is a CDK4/6 inhibitor group, L is a linking group, X is a radiolabel or hydrogen, and n is 1, 2, 3, 4, or 5, and when n is 1, X is a radiolabel, and when n is 2-5, then at least one X is a radiolabel, and upon identification of the individual, the method further comprises further administering to the individual a composition comprising the compound CDK-L-(X)$_n$, wherein CDK is a CDK4/6 inhibitor group, L is a linking group, X is H or a radiolabel and n is 1, 2, 3, 4, or 5, wherein inhibition of growth of the cancer is observed.

In various embodiments, the present disclosure provides methods of imaging a tumor, which comprises administering to an individual a compound of Formula 1 or a composition comprising the compound of Formula 1 and subjecting the individual to PET imaging to obtain an image of the distribution of the compound in the tumor. In various examples, the tumor is a breast tumor and is ER-positive and HER2-negative.

The following are examples of the present disclosure.

Example 1. A compound for non-invasive imaging having the following structure:

CDK-L-(X)$_n$, where CDK is a CDK4/6 inhibitor group, L is a linking group, X is a radiolabel or hydrogen, and n is 1, 2, 3, 4, or 5, and when n is 1, X is a radiolabel, and when n is 2-5, then at least one X is a radiolabel.

Example 2. A compound according to Example 1, where the CDK4/6 inhibitor group is formed from a CDK4/6 inhibitor.

Example 3. A compound according to Example 2, where the CDK4/6 inhibitor group has the following structure:

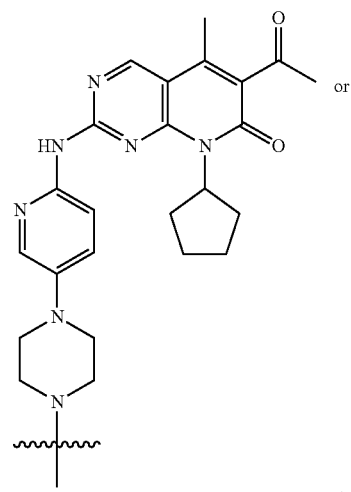

or

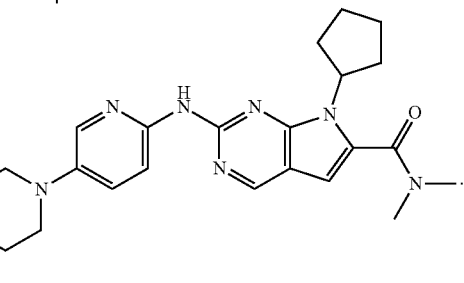

Example 4. A compound according to any one of the preceding Examples, where the linking group has the following structure:

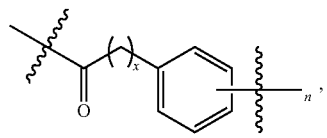

where n is 1, 2, 3, 4, or 5 and x is 0, 1, 2, 3, 4, 5, 6, 7, 8, 9, or 10.

Example 5. A compound according to Example 4, where the linking group has the following structure:

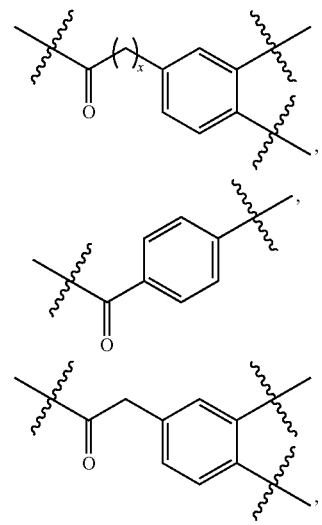

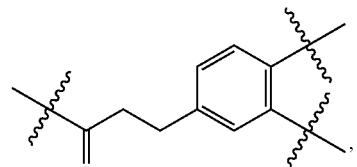

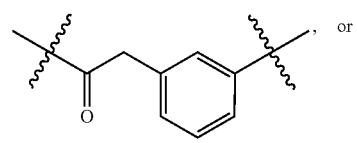

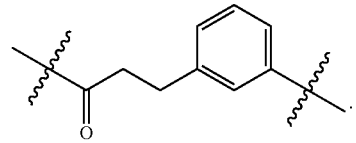

Example 6. A compound according to any one of the preceding Examples, where the radiolabel is chosen from $^{123}$I, $^{124}$I, $^{125}$I, $^{131}$I, $^{211}$At, $^{18}$F and the like, and combinations thereof.

Example 7. A compound according to any one of the preceding Examples, where L-X$_n$ has the following structure:

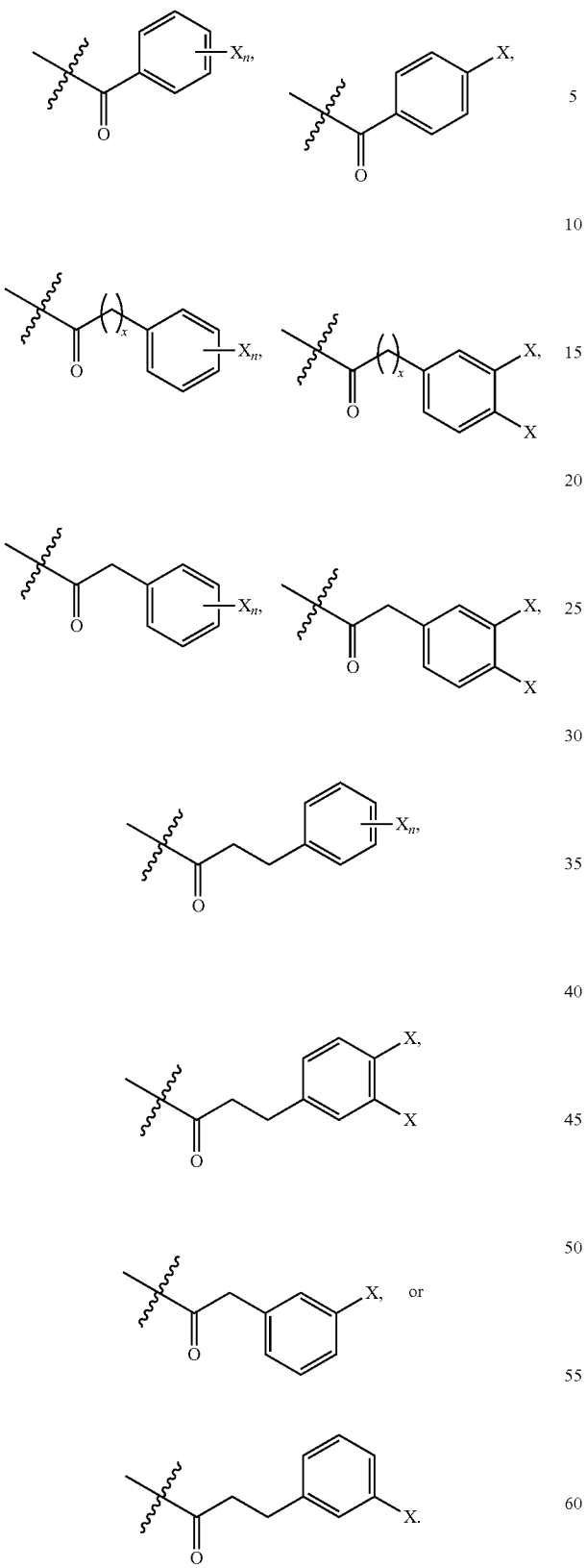

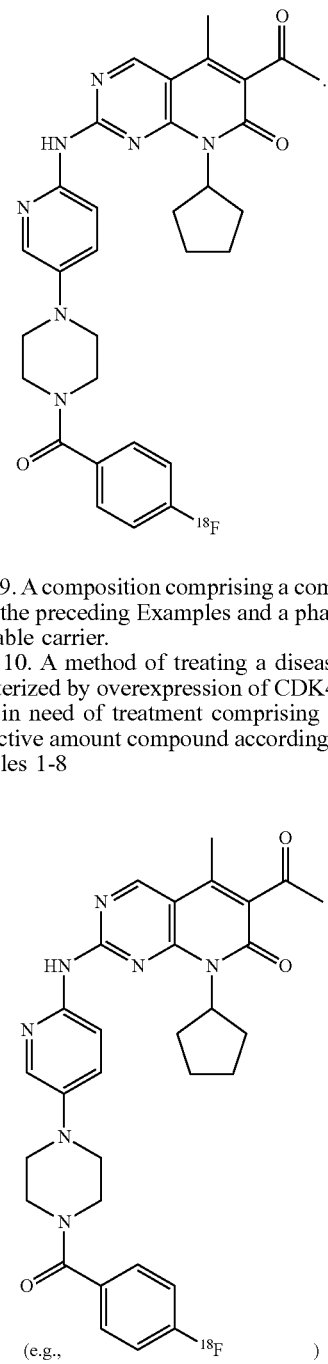

Example 8. A compound according to any one of the preceding Examples, where the compound has the following structure:

Example 9. A composition comprising a compound of any one of the preceding Examples and a pharmaceutically acceptable carrier.

Example 10. A method of treating a disease or disorder characterized by overexpression of CDK4/6 in an individual in need of treatment comprising administering an effective amount compound according to any one of Examples 1-8

(e.g., ...)

or a composition of Example 9.

Example 11. A method according to Example 10, where the disease or disorder is cancer.

Example 12. A method according to Example 11, where the cancer is breast cancer, head and neck cancer, non-small cell lung cancer, melanoma, or glioblastoma.

Example 13. A method according to Example 12, where the cancer is a tumor.

Example 14. A method according to any one of Examples 11-13, the cancer is breast cancer and is ER-positive and HER2-negative.

Example 15. A method according to any one of Examples 10-14, where the compound or composition is used as a tracer.

Example 16. A method according to any one of Examples 10-15, further comprising PET imaging.

Example 17. A method for imaging a tumor, comprising administering to an individual a compound according to any one of Examples 1-8

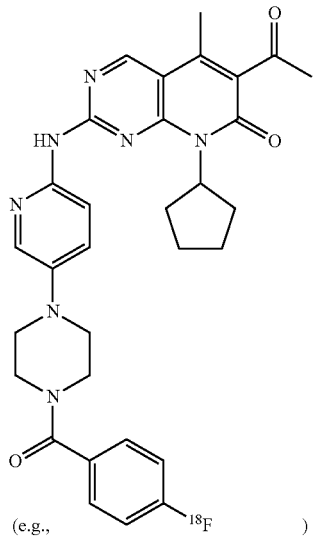 [SMILES: CC(=O)c1c(C)c2cnc(Nc3ccc(N4CCN(C(=O)c5ccc([18F])cc5)CC4)cn3)nc2n(C2CCCC2)c1=O]

(e.g., )

or a composition of Example 9 and subjecting the individual to PET imaging to obtain an image of the distribution of the compound in the tumor (e.g., measuring the distribution of the compound).

Example 18. A method according to Example 17, where the tumor is a breast tumor and is ER-positive and HER2-negative.

Example 19. A method according to Example 17 or Example 18, where the measuring is PET.

Example 20. A method according to any one of Examples 17-20, further comprising using results determined from measuring to determine a therapeutic course of action.

Example 21. A method for treatment of cancer comprising identifying an individual who has a tumor which exhibits accumulation of an administered compound of any one of Example 1-8, and upon identification of the individual, administering a therapeutic composition comprising CDK-L-(X)$_n$, wherein CDK is a CDK4/6 inhibitor group, L is a linking group, X is H or a radiolabel and n is 1, 2, 3, 4, or 5, wherein inhibition of growth of the cancer is observed.

Example 22. A method of Example 21, where the administered compound has the following structure:

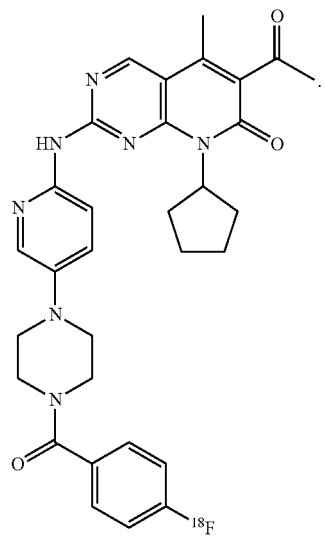 [SMILES: CC(=O)c1c(C)c2cnc(Nc3ccc(N4CCN(C(=O)c5ccc([18F])cc5)CC4)cn3)nc2n(C2CCCC2)c1=O]

The following example is provided for illustrative purposes and not intended to be limiting.

EXAMPLE

The following example describes synthesis and uses of the compounds of the present disclosure.

Herein, we report on the first in vivo CDKi PET imaging agent with strong similarities in pharmacology, potency, and isoform selectivity to Palbociclib, the first clinically FDA approved CDK4/6 inhibitor (*Cancer Discov.* 2015; 5:339-340).

CDK4/6 inhibitors are being intensively studied after the elucidation of the role of cyclin dependent kinases in cell cycle arrest. Several clinical trials were established to study the effects of various compounds in synthetic lethal combination settings (Hamilton et al., *Cancer Treat Rev.* 2016; 45:129-138, Knudsen et al., *Trends Cancer.* 2017; 3:39-55, O'Leary et al., *Nat Rev Clin Oncol.* 2016; 13:417-430). A common characteristic to those treatments is the development of resistance (Knudsen et al., *Trends Cancer.* 2017; 3:39-55, Pandey et al., *Int J Cancer.* 2019; 5:1179-1188, Herrera-Abreu et al., *Cancer Res.* 2016; 76:2301-2313). Poor oral availability, clearance and metabolism, feedback from other cyclins, lack of target enzyme are all hypotheses for the innate and the development of acquired resistance to CDK4/6 inhibitors (Pandey et al., *Int J Cancer.* 2019; 5:1179-1188). However, none of the potential resistance mechanisms demonstrated in preclinical settings could be further confirmed in clinical studies (Knudsen et al., *Trends Cancer.* 2017; 3:39-55, Pandey et al., *Int J Cancer.* 2019; 5:1179-1188). For this reason, we synthesized a radioligand that can reveal whether the drug accumulation in the tumor is limiting the therapeutic efficiency. CDK4/6 targeted imaging using $^{18}$F-CDKi can assist in identifying those patients who will respond to the treatment; moreover, our probe will offer invaluable information on the development of acquired resistance to standard of care CDK4/6 inhibition treatments.

Structurally, the introduction of an $^{18}$F prosthetic synthon to the piperazine group appeared to be a viable approach for generating a labeled CDK4/6 inhibitor. Firstly, we synthesized and profiled $^{19}$F-CDKi, the cold fluorinated analogue of the radiolabeled counterpart. $^{19}$F-CDKi was key to assess if the fluorobenzoic tag would impact the compound's biological activity. $^{18}$F-CDKi was readily synthesized using a modified published synthetic approach (Valeur et al., *Chem Soc Rev.* 2009; 38:606-631, Carney et al., *Mol Imaging Biol.* 2016; 18:386-392). Minor modifications for automation purposes were included as well. Synthesis started from conversion of 4-ethyl-nitrobenzoate to 4-$^{18}$F-fluorobenzoic acid. Subsequent reaction with palbociclib was rapidly accomplished in basic conditions to yield the final $^{18}$F-CDKi imaging agent. Following scale-up synthesis and characterization of the radiotracer, we next tested the radiolabeled tracer $^{18}$F-CDKi both in vitro and in vivo. In light of the relevance of palbocilib in treating ER-positive HER2-negative breast cancer, we chose MCF-7 as a mouse model for our in vitro/in vivo studies.

Initially, we determined the in vivo blood half-life and plasma stability of $^{18}$F-CDKi. The tracer displayed a specific intracellular uptake in MCF-7 cells and an IC$_{50}$ in the nanomolar range similar to the parent compound palbociclib. The insertion of an $^{18}$F prosthetic group did not modify the binding properties of CDKi. Furthermore, as for other CDK4/6 inhibitors, our molecule is also an ATP-competitive ligand of CDK4 and CDK6. The IC$_{50}$ is with single digit nanomolar potency against both CDK4 and CDK6 kinases. The blood half-life, following a single bolus intravenous injection, showed a biphasic pharmacokinetic profile with rapid elimination of $^{18}$F-CDKi during the first 10 min. $^{18}$F-CDKi shows a marked lipophilic behavior and more than 98% of the tracer was stable in vivo at 4 h p.i. In subcutaneous MCF-7 xenografts, $^{18}$F-CDKi was rapidly washed out from non-target organs resulting in a remarkable tumor-to-non-target tissue at 2 h post-injection. Consistent with CDKi activation and cycD1 overexpression in breast tumors, $^{18}$F-CDKi was observed to specifically accumulate in the tumor as proven by the blocking experiment. MCF-7 bearing mice that received an injection of palbociclib prior to the radiotracer showed negligible $^{18}$F-CDKi tumor uptake. It is considered that more clinical positive outcomes may result using the present compound.

The cell cycle is a progression of four distinct phases (G1, S, G2, M), with various cycle proteins being essential in regulating this process. We aimed to develop a radiolabeled Cyclin Dependent Kinase 4/6 (CDK4/6) inhibitor for breast cancer imaging. Our transfluorinated analog ($^{18}$F-CDKi) was evaluated and validated as a novel PET imaging agent to quantify CDK4/6 expression in ER-positive HER2-negative breast cancer. Methods: $^{18}$F-CDKi was synthesized and assayed against CDK4/6 kinases. $^{18}$F-CDKi was prepared with a 2-step automated synthetic strategy that yielded the final product with remarkable purity and molar activity. In vitro/in vivo biologic specificity was assessed in a MCF-7 cell line and in mice bearing MCF-7 breast tumors. Non-radioactive palbociclib (Inbrance, Pfizer®) was used as blocking agent to investigate the binding specificity and selectivity of $^{18}$F-CDKi. Results: $^{18}$F-CDKi was obtained with an overall radiochemical uncorrected yield of 15% and radiochemical purity>98%. The total synthesis time from the start of synthesis to final injectable formulated tracer is 70 minutes. The retention time reported for $^{18}$F-CDKi and $^{19}$F-CDKi is 27.4 min as demonstrated by co-injection with $^{19}$F-CDKi in a HPLC. In vivo blood half-life [$t_{1/2}$ (weighted)= 7.03 minutes], and octanol/water phase partition coefficient (log $D_{O/W}$=1.91±0.24) showed a mainly lipophilic behavior. $^{18}$F-CDKi is stable in vitro and in vivo (>98% at 4 h post injection) and maintained its potent targeting affinity to CDK4/6. Cellular uptake experiments performed in the MCF-7 breast cancer cell line (ER-positive/HER$_2$-negative) demonstrated specific uptake with a maximum intracellular concentration of ~65% as early as 10 minutes post incubation. The tracer uptake was reduced to <5% when cells were co-incubated with a molar excess of Palbociclib. In vivo imaging and ex-vivo biodistribution of ER-positive/HER-2 negative MCF-7 breast cancer models showed a ~4% ID/g tumor specific uptake (reduced to ~0.3% ID/g with a 50-fold excess of cold palbociclib). A comprehensive biodistribution analysis also revealed a significantly lower activation of CDK4/6 in non-targeting organs. Conclusion: $^{18}$F-CDKi represents the first $^{18}$F positron emission tomography (PET) CDK4/6 imaging agent and a promising imaging agent for ER-positive HER2-negative breast cancer.

We developed $^{18}$F-CDKi, a PET radiolabeled version of Palbociclib (Inbrance®, Pfizer) with the aim to image non-invasively kinase expression in an animal model of breast cancer. Specifically, we introduced an F-18 prosthetic group ($^{18}$F-fluorobenzoic acid, $^{18}$F-FBA), on the terminal piperazine and synthesized a novel PET active functional molecule. In this paper, our goal was to determine if i) $^{18}$F-CDKi has suitable pharmacokinetic properties for non-invasive PET imaging and ii) whether the tracer is selective for CDK4/6 in vitro and in vivo. For both in vitro as well as in vivo evaluation, a human breast cancer ER-positive, HER2-negative cell line (MCF-7) was used.

This radiolabeled inhibitor is able to target specifically CDK4/6. Because of these promising results in mouse models, we anticipate $^{18}$F-CDKi to have a high prognostic value for tumor imaging and treatment response monitoring.

MATERIALS AND METHODS

Materials

No carrier added $^{18}$F-fluoride was produced by the (p,n) reaction of [$^{18}$O]H$_2$O (89% isotopic purity, PETNET; Knoxville, TN, USA) in an RDS-112 cyclotron (Siemens; Knoxville, TN) using a 2.7 mL target. Potassium carbonate, kryptofix, ethyl 4-nitrobenzoate, N,N,N',N'-Tetramethyl-O-(1H-benzotriazol-1-yl)uronium hexafluorophosphate (HBTU), triethylamine, ammonium formate, sodium hydroxide, hydrochloric acid, dimethyl sulfoxide-d$_6$, anhydrous acetonitrile and anhydrous dimethyl sulfoxide were purchased from Millipore-Sigma (Milwaukee, WI, USA) and used without further purification unless otherwise stated. Palbociclib hydrochloride was purchased from Selleck (Houston, TX). ATP was obtained from PerkinElmer (Boston, MA). Absolute ethanol was purchased from Thermo Fisher (Waltham, MA). Sep-Pak Accell Plus QMA and C18 sep-pak cartridges were purchased from Waters (Milford, MA). Semi-preparative high-pressure liquid chromatography (HPLC) was conducted in the GE TRACER-lab™ FX2N under the following HPLC conditions: Phenomenex Gemini C6 phenyl column, 10×250 mm, 10 μm; mobile phase: 64% 75 mM AMF and 36% MeCN; 5 mL/min (Method A). The FX2N is equipped with an S1122 Sykam solvent delivery system. Analytical HPLC was performed using a Shimadzu binary LC-20AR HPLC gradient pump with an inline SPD-20A variable wavelength UV/VIS detector, and an E&Z flow count unit with a PMT detector using a Phenomenex C6 Gemini reverse-phase column, 4.6×250 mm 5 μm with a mobile phase of 64% 75 mM AMF and 36% MeCN; 2 mL/min (Method B). Analytical chromatograms were collected by an analog-to-digital converter using Lab Solutions software. Preparative and analytical HPLC analyses of $^{18}$F-labeled compounds were calibrated with the corresponding $^{19}$F analogues. Radioactivity in blood half-life, cell uptake and biodistribution studies was quantified with a WIZARD² automatic γ-counter (PerkinElmer, Boston, MA). Radioactivity in blood half-life, cell uptake and biodistribution studies was quantified with Inveon PET/CT (Siemens Medical Solutions, Knoxville, TN) and reconstructed using Inveon Research (Siemens Medical Solutions, Knoxville, TX). All F-18 and F-19 CDKi final products were formulated in 10% Ethanol/90% Saline 0.9%.

Cell Culture

Phosphate buffered saline (PBS) and Dulbecco's Modified Eagle Medium (DMEM) were purchased from Thermo Fisher (Waltham, MA). MCF-7, a human ER-positive, HER2-negative breast cancer cell line was purchased from ATCC (Manassas, VA). DMEM contained 10% (vol/vol) heat inactivated fetal bovine serum, 100 IU penicillin, and 100 µg/mL streptomycin.

Mouse Model

Female athymic nude CrTac:NCr-Foxnlnu mice (n=35) were purchased from Taconic Laboratories (Hudson, NY). 20 mice received subcutaneous injections with 2×10⁶ human MCF-7 cancer cells in Matrigel® (BD Biosciences, San Jose, CA) into each right shoulder and were allowed to grow for approximately two months until the tumors reached ~10 mm in diameter. All mice were supplemented with 60 days 0.72 mg slow release estradiol pellets purchased from Innovative Research of America (IRA, Sarasota, FL) implanted in the left flank. Mice were anesthetized (isoflurane 1.5%, 2 L/min medical air) during tumor implantation and microPET imaging.

15 mice were used for blood half-life measurements and in vivo stability studies. All animal experiments were conducted in accordance with protocols approved by the Institutional Animal Care and Use Committee of NYU Langone Health and followed NIH guidelines for animal welfare.

Preparation of $^{19}$F-CDKi

To a solution of palbociclib in DMSO (20 mg, 0.04 mmol), fluorobenzoic acid (15 mg, 0.1 mmol), HBTU (45 mg, 0.1 mmol) and triethylamine (12 mg, 0.1 mmol) were added and the solution reacted at 37° C. for 24 hours. The resulting solution was filtered and purified by reverse phase HPLC to the desired derivative (yield=70%), dried and lyophilized to yield the final product. Electrospray ionization mass spectrometry (ESI-MS) spectra were recorded with a Shimadzu LC-2020 with electrospray ionization SQ detector.

Radiochemistry

No-carrier-added (n.c.a.) $^{18}$F-fluoride was obtained via the $^{18}$O(p,n)$^{18}$F nuclear reaction of 11-MeV protons in a RDS Eclypse (Siemens Medical Solutions, Knoxville, TN) using enriched $^{18}$O-water. Synthesis was completely automated using a FX2N module (GE Healthcare, Chicago, IL). Briefly, a QMA cartridge containing cyclotron-produced $^{18}$F fluoride ion was eluted with a solution containing 9 mg Kryptofix [2.2.2] (4,7,13,16,21,24-hexaoxa-1,10-diazabicyclo[8.8.8]hexacosane), 0.08 mL 0.15 M $K_2CO_3$ and 1.92 mL MeCN into a 5 mL reaction vial. Water was removed azeotropically at 120° C. 1 mg of ethyl 4-nitrobenzoate was dissolved in 300 µL of DMSO was then added to the reaction vial and heated to 150° C. for 15 minutes and then cooled to room temperature. Following, 150 µL of 1M NaOH was added. The reaction mixture was stirred for 1 min and 150 µL of 1M HCl was added to quench. Then, 2 mg of Palbociclib dissolved in 200 µL of DMSO was added followed by 10 mg of HBTU dissolved in 200 µL of DMSO and 30 µL of $Et_3N$. The reaction mixture was stirred for 1 minute. 400 µL MeCN followed by 700 µL $H_2O$ was then added and the solution was injected onto a C6-Phenyl analytical HPLC column and eluted under isocratic conditions. For intravenous administration, the product-containing fraction was passed through a C18 light-SepPak® cartridge preconditioned with EtOH (10 mL) and water (10 mL). The cartridge was washed with water (3 mL) and $^{18}$F-CDKi was eluted using EtOH (400 µL). The solution was then diluted with 0.9% saline to 10% EtOH. The radiochemical purity of the final formulation was confirmed using analytical HPLC (Method B: the final product was eluted at $t_R$=17 min). Co-elution with nonradioactive F-19 reference compound confirmed the identity of the radiotracer. Specific activity was determined by dividing the activity present in the final formulated product (GBq) by the material remaining in the formulated product after purification (moles) and was determined using a UV calibration curve (λ=254 nm).

Chemical Hydrophobicity Index and Octanol/Water Partition Coefficient

The Chemical Hydrophobicity Indices (CHI) were measured using a previously developed procedure (Valkó, *Journal Chromatogr A*. 2004; 1037:299-310, Valkó et al., *Anal Chem*. 1997; 69:2022-2029. Briefly, reverse phase HPLC was used to measure the retention times of a set of standards with known CHI. A standard curve was then created to calculate the CHI of $^{19}$F-CDKi based on the HPLC retention time. The lipophilicity of the $^{18}$F-CDKi was acquired by adding 0.09 mBq to a mixture of 0.5 mL of 1-octanol and 0.5 mL of 25 mM phosphate buffered saline (pH 7.4) and mixed for 5 minutes. Then, the mixture was centrifuged at 15.000 rpm for 5 minutes. 100 µL samples were obtained from organic and aqueous layers, and the radioactivity of the samples were measured in a WIZARD² automatic γ-counter. The experiment was performed in triplicate, and the resulting log $P_{ow}$ was calculated as the mean±SD.

Blood Half-Life

The blood half-life of $^{18}$F-CDKi was calculated by measuring the activity of blood samples collected at different time points p.i. (5, 15, 30, 45, 60, 90 and 120 minutes). Female nude mice (n=3) were injected via lateral tail vein with $^{18}$F-CDKi (and blood samples obtained by retro-orbital bleed using tared capillary tubes. Samples were weighed, and activity was measured by γ-counter. The blood half-life was calculated using Graph Prism 7 (GraphPad Software, La Jolla, CA) using a two-phase decay least squares fitting method and expressed as % ID/g.

In Vivo/Ex Vivo Blood Stability $^{18}$F-CDKi (7.4 mBq) was injected in healthy athymic nude mice (n=15) via tail injection. Mice were sacrificed at different time points (0, 60, 120, 180, 240 min p.i.) and blood was collected. 750 µL of MeCN were added to the collected blood, then centrifuged (5 minutes at 5000 rpm) to pellet blood cells and proteins. The supernatant was collected, diluted with 750 μL of H$_2$O and injected onto a HPLC. The blood stability was measured by HPLC analysis (Method B).

IC50 Binding Affinity and Competitive Inhibitory Displacement

IC$_{50}$ values were determined using a competitive ATP quantitative assay. $^{19}$F-CDKi. MCF-7 cells were cultured at 37° C. for 4 h. Then, $^{19}$F-CDKi or vehicle was added at different concentration and incubated at 37° C. for 96 h. Cell viability was then assessed using CellTiter-Glo® Luminescent Assay (Promega, Madison, WI), used accordingly to manufacturer's guidelines. Cell viability inhibition (%) was calculated according to the formula [1−(mean luminosity of treated sample/mean luminosity of vehicle control)]×100. IC$_{50}$ for growth or viability inhibition was calculated using Graph Prism 8 (GraphPad Software Inc, La Jolla, CA). We used $^{18}$F-CDKi and palbobiclib for competitive displacement studies. MCF-7 cells were seeded in a 12 wells plate (1×10$^5$ cells 24 h prior the experiment). The next day, a fixed concentration of $^{18}$F-CDKi (50 nM) was co-incubated with linearly doubling concentrations of palbociclib (from 0 to 500 nM) at 37° C. for 2 h. Then, the cells were washed twice with PBS, lysed with 1N NaOH, and the activity (CPM) measured in a γ-counter for bound $^{18}$F radioligand. The percentage of bound radioligand was finally plotted against palbociclib concentration. Competitive displacement curves were fitted using Graph Prism 8 (GraphPad Software Inc, La Jolla, CA).

In Vitro Uptake

MCF-7 cells were seeded in a 6 well plates (5×10$^6$ cells 24 hours prior the experiment). The next day, $^{18}$F-CDKi was added alone or together with a 50-fold excess Palbociclib and incubated at 37° C. for 1 h. After 1 h, cells were firstly washed three times with PBS, then lysed with 1N NaOH, and finally media and cells counted in a γ-counter. The percentage of bound/unbound radioligand at each time point was measured in triplicate and plotted as a function of time.

MicroPET/CT Imaging

Twelve subcutaneous MCF-7 implanted athymic nude mice were divided in two groups (blocked and unblocked) and administered with $^{18}$F-CDKi (~7.4 mBq) via tail vein injection. Approximately 5 min prior to PET acquisition, mice were anesthetized by inhalation of a mixture of isoflurane (Baxter Healthcare, Deerfield, IL, USA; 2% isoflurane, 2 L/min medical air) and positioned on the scanner bed. Anesthesia was maintained using a 1% isoflurane/O$_2$ mixture. PET data for each mouse was recorded and acquired at 30 min p.i and at 120 min p.i. Blocking studies were performed after a pre-injection of 50-fold excess palbociclib (8.4 nmol, 3.8 μg, 30 min before). The duration of the microPET/CT imaging sessions was 20 min each.

Biodistribution

Biodistribution of $^{18}$F-CDKi was performed in subcutaneous MCF-7 bearing athymic nude mice (n=8). Mice were divided (n=4/group) in blocked and unblocked (50-fold excess palbociclib, 30 minutes before) and administered with $^{18}$F-CDKi via tail vein injection (1.85 mBq). At 120 minutes post injection of the radioligand, the mice were sacrificed and organs of interest were collected. Organs were weighed, and activity was measured with a WIZARD$^2$ automatic γ-counter (PerkinElmer, Boston, MA). The radiopharmaceutical uptake was expressed as a percentage of injected dose per gram (% ID/g) using the following formula: [(activity in the target organ/grams of tissue)/injected dose]×100%.

Statistical Analysis

All data are expressed as mean±SD. Differences between mouse cohorts were analyzed with the 2-tailed unpaired Student's t-test and were considered statistically significant when P<0.05.

RESULTS

Chemistry and Radiochemistry

Figure 5:
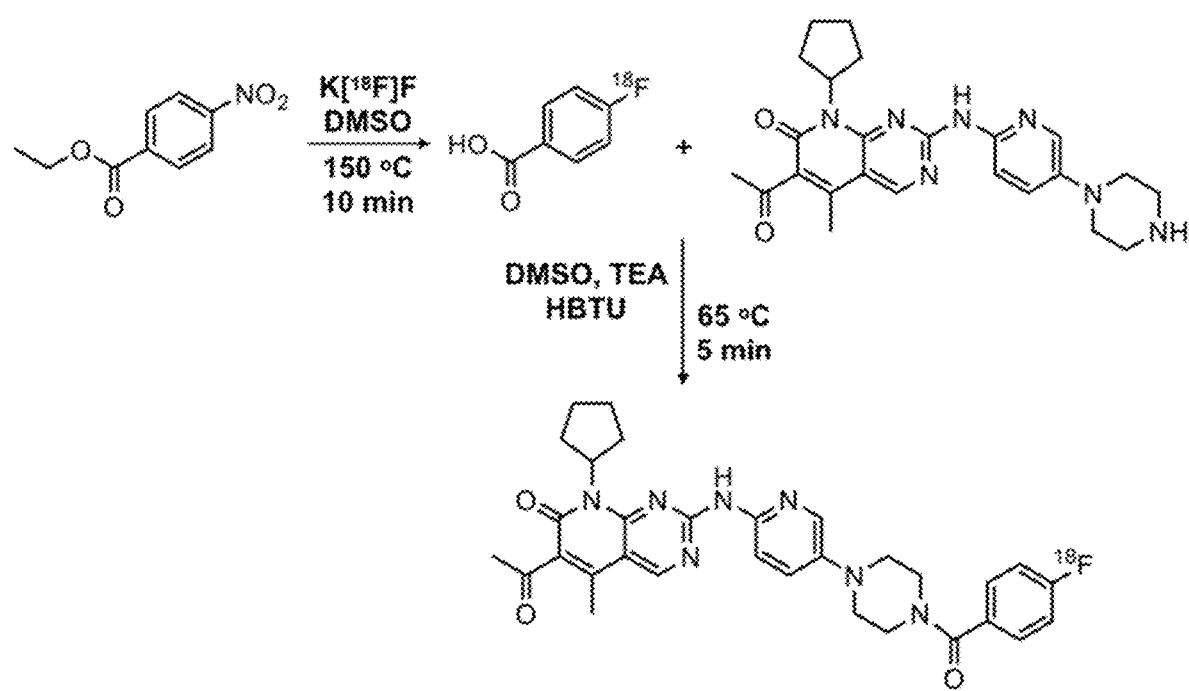
FIG. 5 shows a synthetic path for $^{18}$F-CDKi.
Figure 6:
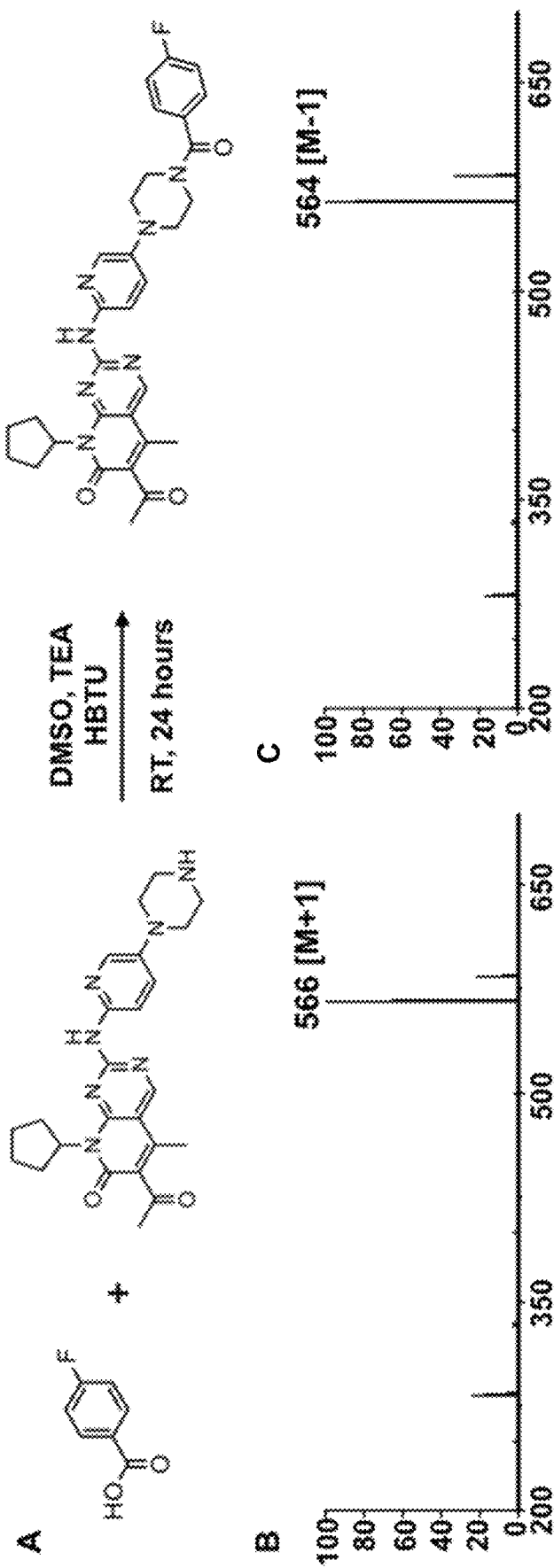
FIG. 6 shows (A) a synthetic path for $^{19}$F-CDKi. Mass spectrum (B) in positive mode and (C) negative mode for $^{19}$F-CDKi.
Figure 7:
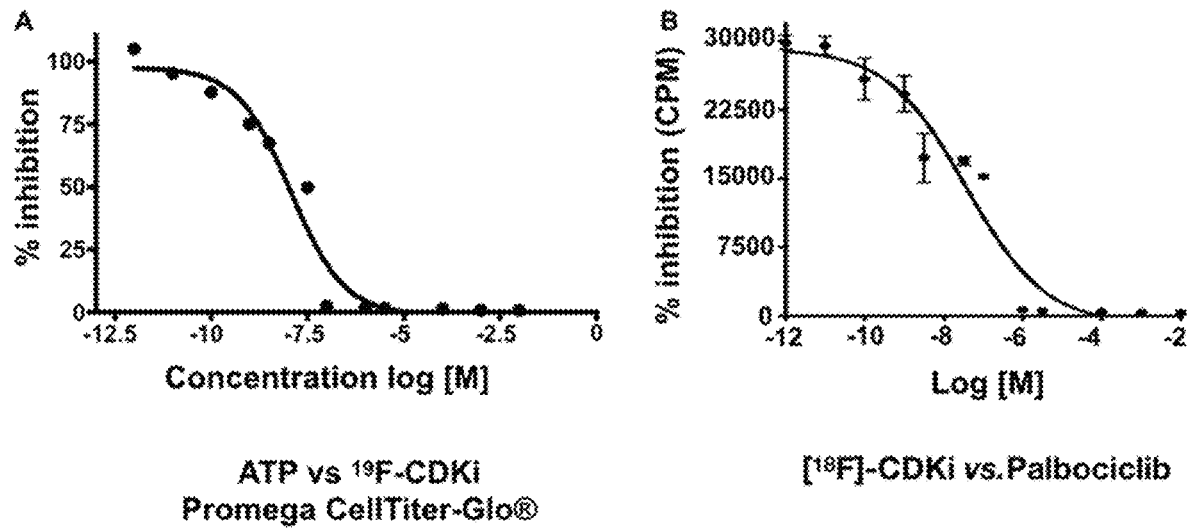
FIG. 7 shows competitive displacement of $^{19}$F-CDKi vs ATP and $^{18}$F-CDKi vs palbociclib in MCF-7 cells.

Synthetic routes for the non-radioactive compound $^{19}$F-CDKi and mass spectrometry analysis are shown in FIG. 6. $^{18}$F-CDKi was synthesized by a 2-steps method (FIGS. 1A and B and FIG. 5). The final F-18 transfluorinated product was obtained with an overall uncorrected yield of ~15% (n=4) and a radiochemical purity>98%. Specific activity was 44 GBq/μmol and the total automated synthesis time is 80-90 minutes. The retention time reported for $^{18}$F-CDKi and [$^{19}$F]-CDKi is ~17 min as demonstrated by co-injection with $^{19}$F-CDKi in a HPLC (FIG. 1C). $^{19}$F-CDKi was obtained by reacting palbociclib and 4-fluorobenzoic acid at RT for 24 h. Final yield after HPLC purification was ~80%. $^{19}$F-CDKi was assessed by LC-MS with a high purity as shown by both positive and negative spectrum. Observed m/z for $^{19}$F-CDKi was 566 ([M]+H) and 564 ([M]−H) in positive and negative polarity mode (expected m/z for $^{19}$F-CDKi=565) (FIGS. 6B and 6C). No unreacted palbociclib (mw=447.5 g/mol) was observed after purification indicating a high chemical purity of the HPLC purified $^{19}$F-CDKi.

Figure 2:
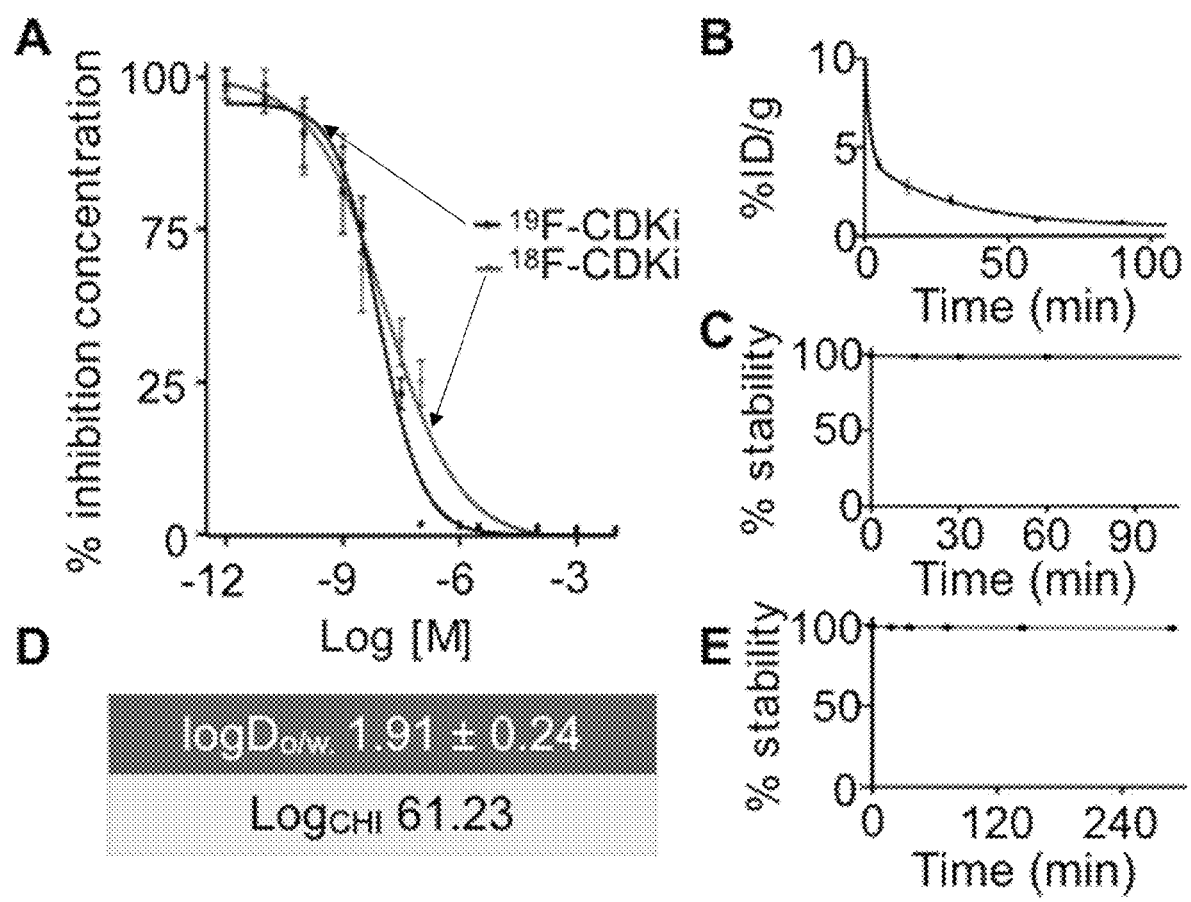
FIG. 2 shows $^{18}$F-CDKi/$^{19}$F-CDKi shows nanomolar binding affinity to CDK4/6 (A). $^{18}$F-CDKi displays a 7 minutes blood half-life (B), high in vitro and in vivo stability (C and D) and lipophilic behavior (E).
Figure 8:
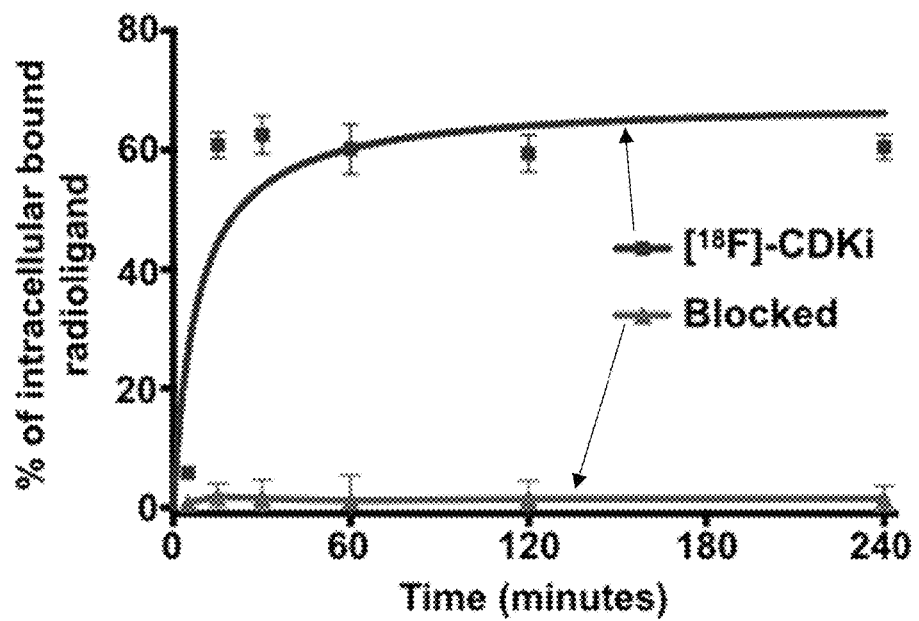
FIG. 8 shows cell-associated uptake of $^{18}$F-CDKi.

Cellular Binding Specificity and Cell Internalization $^{18}$F-CDKi maintained a potent targeting affinity to CDK4/6 (~13 nM) (FIG. 2A). The competitive displacement of palbociclib in MCF-7 cells was an indication of the similar inhibition effect of $^{18}$F-CDKi to $^{19}$F-CDKi (~18 nM) in MCF-7 cells (Supplemental FIGS. 3A, 3B). Cell-associated uptake of $^{18}$F-CDKi is shown in FIG. 8. Cell uptake could be blocked nearly completely (>98%) by addition of an excess of cold, unlabeled palbociclib (P<0.0001) suggesting the high cellular specificity of $^{18}$F-CDKi. Cellular uptake experiments performed in MCF-7 breast cancer cell line (ER-positive/HER$_2$-negative) demonstrated a maximum intracellular concentration of ~65% at already 10 minutes post incubation, when the internalization rate reached a plateau.

Stability and Pharmacokinetics

The in vivo blood half-life [t$_{1/2}$(weighted)] was 7.03 minutes (FIG. 2B). $^{18}$F-CDKi was stable in both in vitro and in vivo with more than 98% of the parent compound intact after 4 h of incubation (>98% at 4 h post injection, FIGS. 2C and D). Octanol/water phase partition coefficient (log D$_{O/W}$) is 1.91±0.24.

In Vivo Imaging and Ex-Vivo Biodistribution

Figure 3:
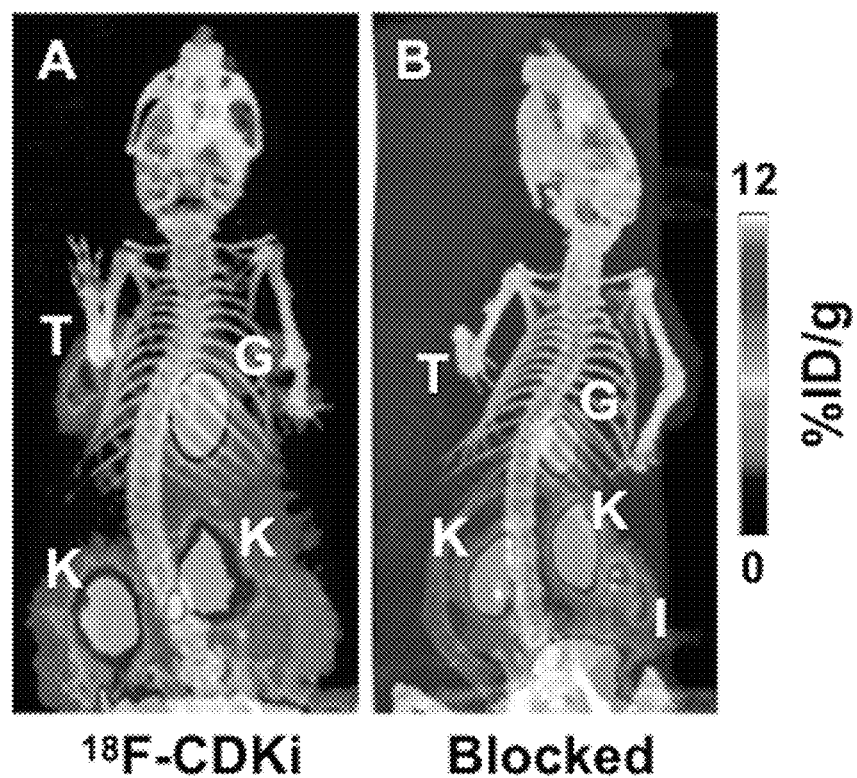
FIG. 3 shows in vivo microPET/CT of MCF-7 bearing mouse models. Left panel shows a single one-bolus injection of $^{18}$F-CDKi (7.4 mBq acquired at 2 h p.i.). Right panel shows a control MCF-7 mouse (pre-injected with an excess of palbociclib 30 min prior to $^{18}$F-CDKi, 7.4 mBq acquired at 2 h p.i.). Active areas in scans, from top to bottom, are nasal epithelium and Harderian glands, tumor (T), gallbladder (G), kidneys (K) and intestines (I).
Figure 4:
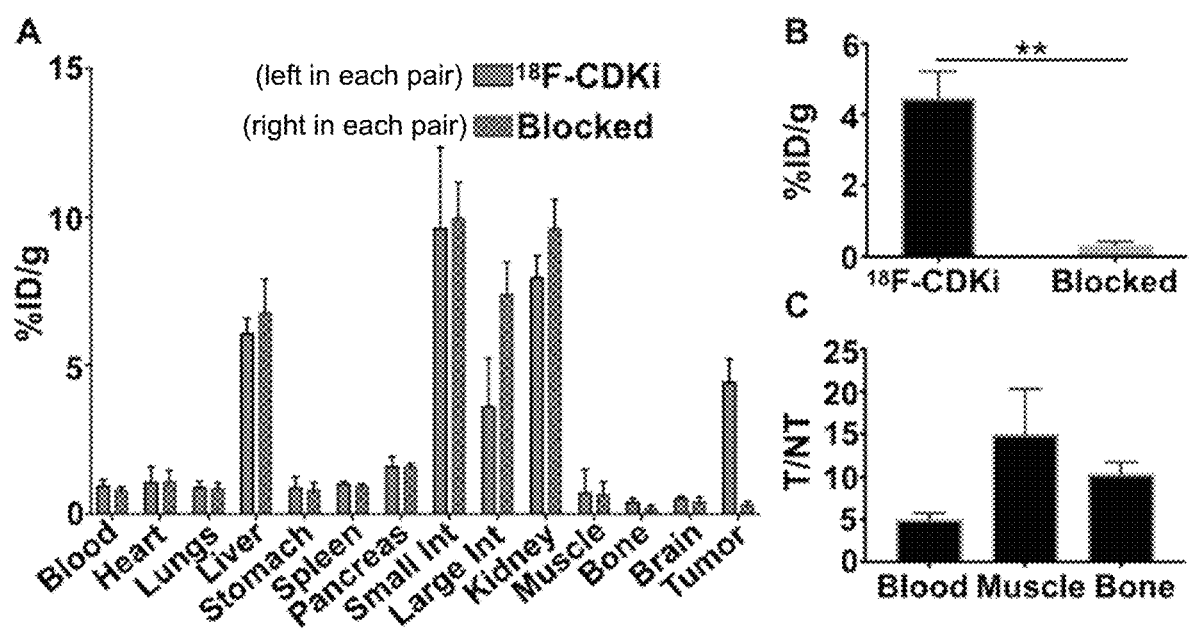
FIG. 4 shows (A) ex-vivo biodistribution (2 h p.i.) with a single $^{18}$F-CDKi or with a pre-injection of palbociclib (blocked). (B) shows the significance in tumor % ID/g between $^{18}$F-CDKi and blocked control group and (C) a representation of tumor-to-non-target blood, -muscle, or -bone ratio (n=4).
Figure 9:
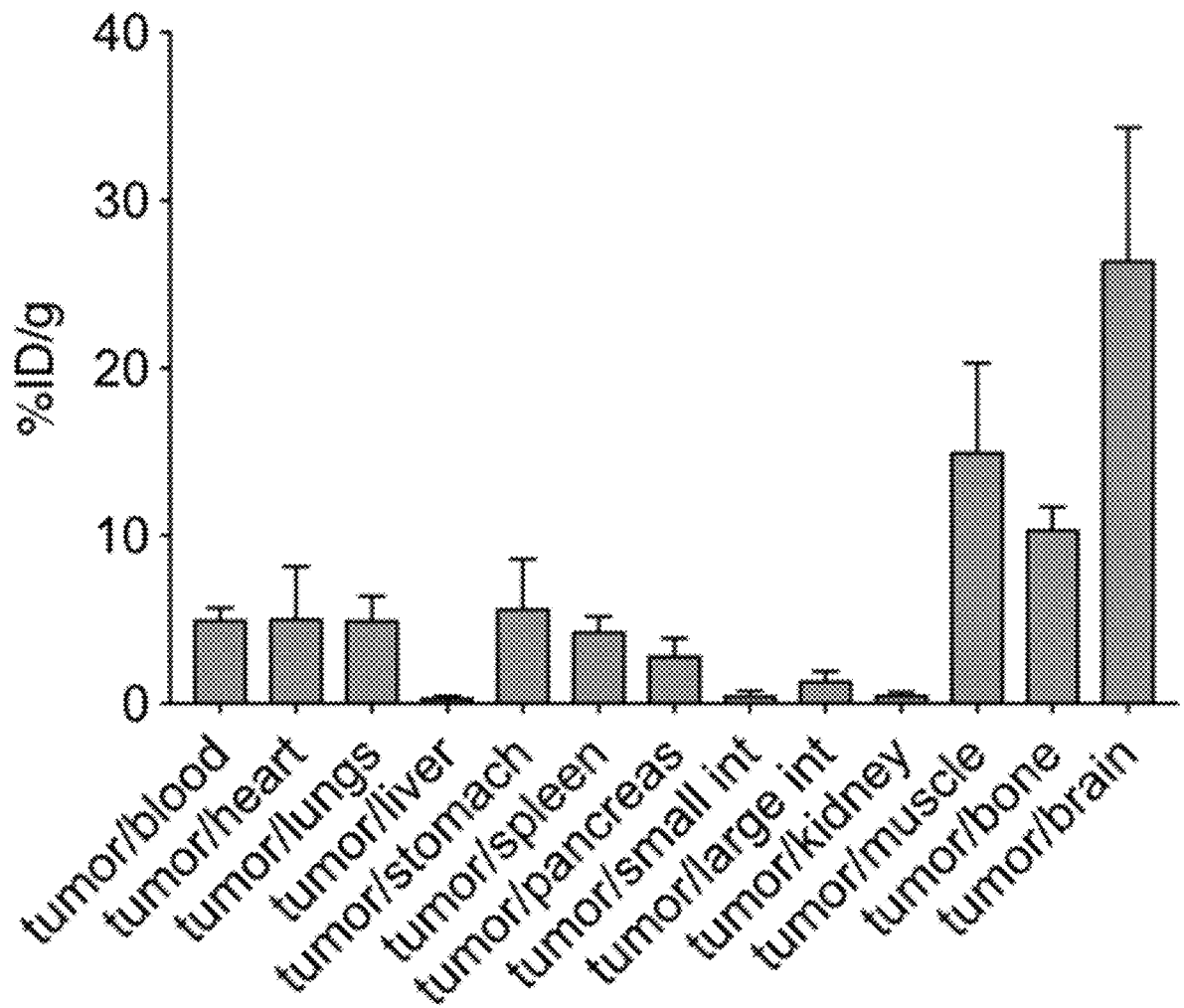
FIG. 9 shows the in vivo PK profile of $^{18}$F-CDKi.

PET imaging in ER-positive/HER-2 negative MCF-7 breast cancer models showed a significant specific uptake in the tumor lesion. (FIG. 3). MCF-7 xenografts showed a ~4% ID/g (FIG. 4A) when mice were injected with $^{18}$F-CDKi. Tracer uptake in the tumor decrease to ~0.3% ID/g (FIG. 4B) when mice were blocked with a 50-fold excess of palbociclib (8.4 nmol, 3.8 μg). PET imaging and biodistribution data showed that $^{18}$F-CDKi is cleared via the hepatobiliary route (FIGS. 3 and 4A). High concentration of $^{18}$F-CDKi were found in the kidney (7.99±0.7 or 9.6±0.98% ID/g), liver (6±0.5 or 6.77±1.15% ID/g) and small intestines (9.6±2.7 or 10±1.19% ID/g) with relatively low distribution in other tissues (FIG. 4A) at 2 h post injection. A comprehensive biodistribution analysis revealed also a remarkable tumor-to-blood (>5), tumor-to-muscle (>15) and tumor-to-bone (>10) ratio (FIG. 4C). A complete dataset showing a favorable—is available in the Supplemental information (FIG. 9).

The preceding description provides specific examples of the present disclosure. Those skilled in the art will recognize that routine modifications to these embodiments can be made which are intended to be within the scope of the disclosure.

What is claimed is:

1. A compound for non-invasive imaging having the following structure:

CDK-L-(X)$_n$, wherein

CDK is a CDK4/6 inhibitor group having the following structure:

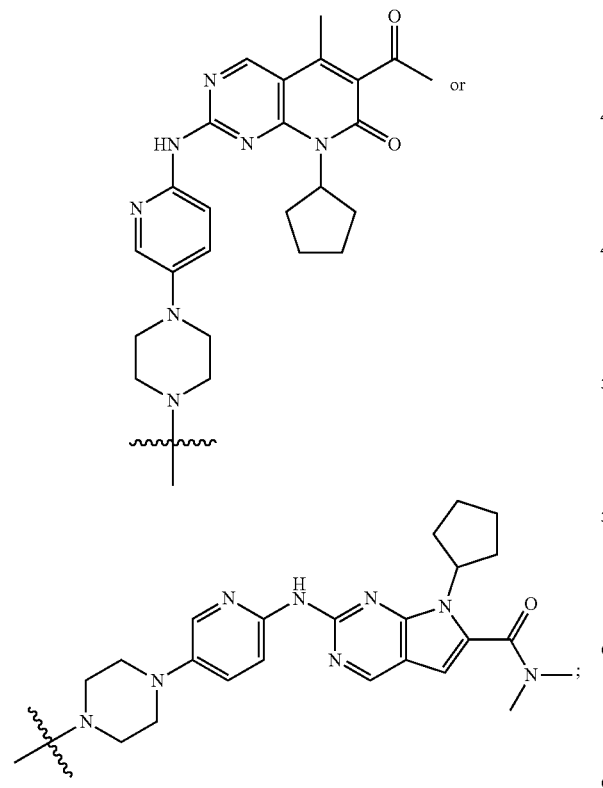

or

L is a linking group having the following structure:

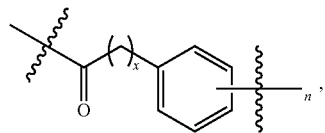

where n is 1, 2, 3, 4, or 5 and x is 0, 1, 2, 3, 4, 5, 6, 7, 8, 9, or 10;

X is a radiolabel or hydrogen, n is 1, 2, 3, 4, or 5, and when n is 1, X is a radiolabel, and when n is 2-5, then at least one X is a radiolabel.

2. The compound of claim 1, wherein the CDK4/6 inhibitor group is formed from a CDK4/6 inhibitor.

3. The compound of claim 1, wherein the linking group has the following structure:

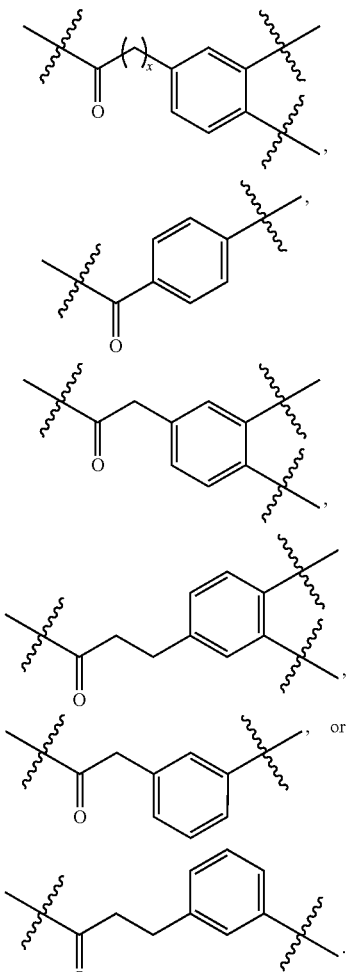

4. The compound of claim 1, wherein the radiolabel is chosen from $^{123}$I, $^{124}$I, $^{125}$I, $^{131}$I, $^{211}$At, $^{18}$F, and combinations thereof.

5. The compound of claim 1, wherein L-X$_n$ has the following structure:

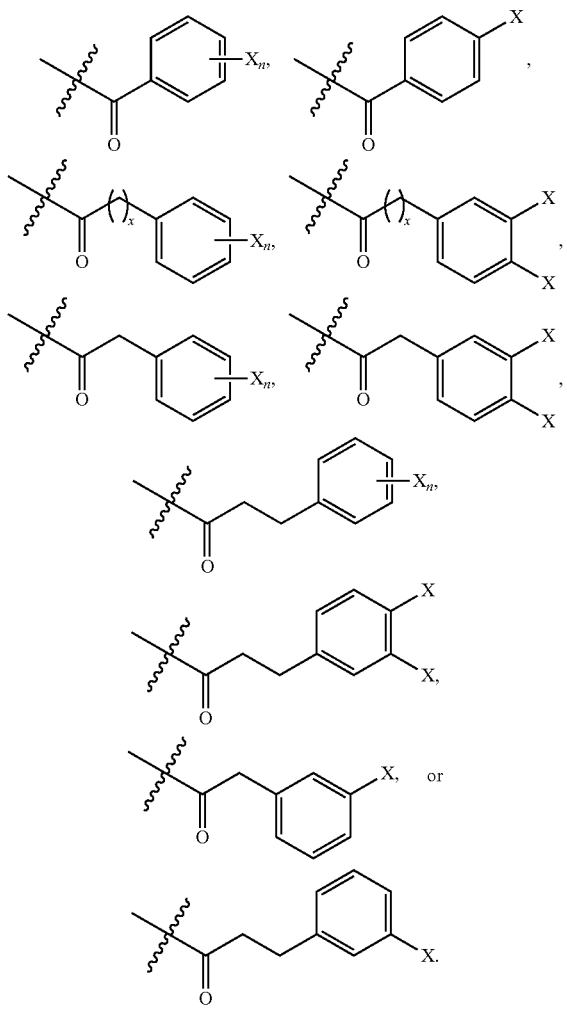

6. The compound of claim 1, wherein the compound has the following structure:

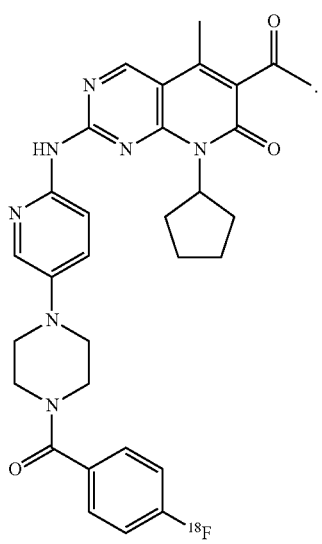 [SMILES: CC(=O)c1c(C)c2cnc(Nc3ccc(N4CCN(C(=O)c5ccc([18F])cc5)CC4)cn3)nc2n(C2CCCC2)c1=O]

7. A composition comprising a compound of claim 1 and a pharmaceutically acceptable carrier.

8. A method of treating a disease or disorder characterized by overexpression of CDK4/6 in an individual in need of treatment comprising administering an effective amount of a compound of claim 1 or a composition comprising an effective amount of a compound of claim 1.

9. The method of claim 8, wherein the disease or disorder is cancer.

10. The method of claim 9, wherein the cancer is breast cancer, head and neck cancer, non-small cell lung cancer, melanoma, or glioblastoma.

11. The method of claim 9, the cancer is breast cancer and is ER-positive and HER2-negative.

12. The method of claim 8, further comprising PET imaging.

13. The method of claim 8, wherein the compound has the following structure:

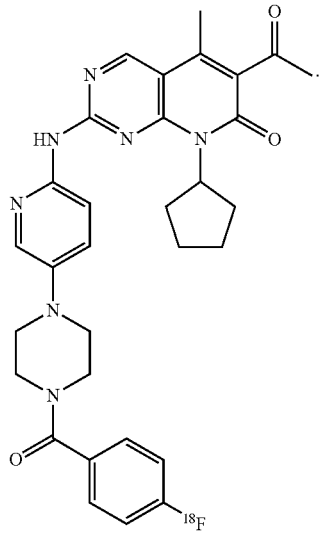

14. A method for imaging a tumor, comprising administering to an individual a compound of claim 1 or a composition comprising a compound of claim 1, and subjecting the individual to PET imaging to obtain an image of the distribution of the compound in the tumor.

15. The method of claim 14, wherein the tumor is a breast tumor and is ER-positive and HER2-negative.

16. The method of claim 14, wherein the compound has the following structure:

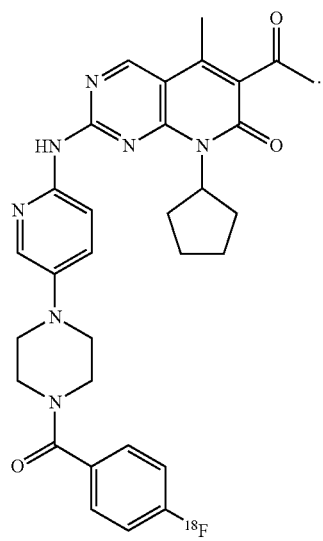 [SMILES: CC(=O)c1c(C)c2cnc(Nc3ccc(N4CCN(C(=O)c5ccc([18F])cc5)CC4)cn3)nc2n(C2CCCC2)c1=O]

17. A method for treatment of cancer comprising identifying an individual who has a tumor which exhibits accumulation of an administered compound of claim 1, and upon identification of the individual, administering a therapeutic composition comprising CDK-L-(X)$_n$, wherein
CDK is a CDK4/6 inhibitor group having the following structure:

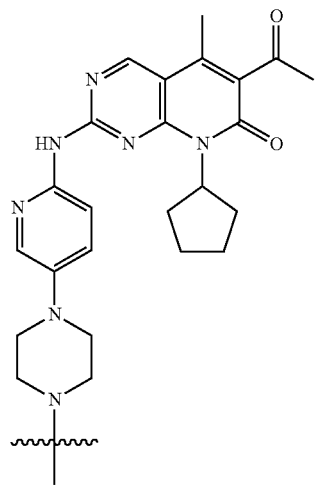

or

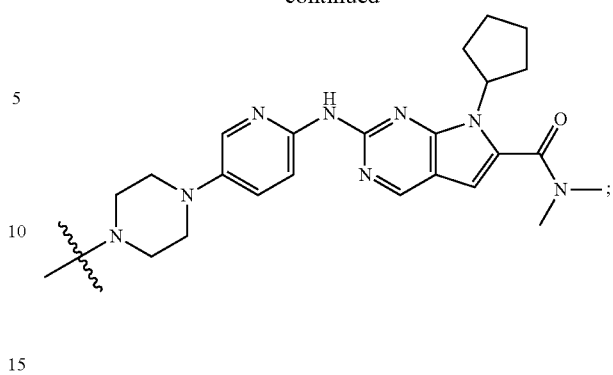

L is a linking group; and
X is H or a radiolabel and n is 1, 2, 3, 4, or 5;
wherein inhibition of growth of the cancer is observed.

18. The method of claim 17, wherein the administered compound has the following structure:

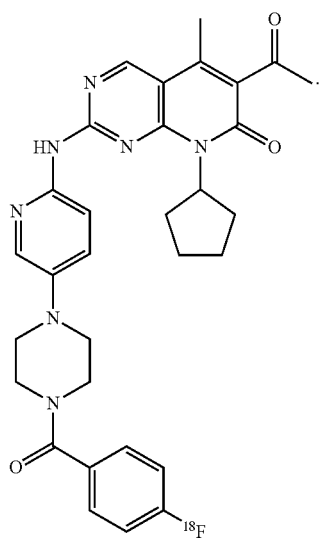

* * * * *